United States Patent
Goshgarian et al.

(10) Patent No.: US 9,649,381 B2
(45) Date of Patent: May 16, 2017

(54) TRANSPORTER PROTEIN-COUPLED NANODEVICES FOR TARGETED DRUG DELIVERY

(71) Applicant: Wayne State University, Detroit, MI (US)

(72) Inventors: Harry Goshgarian, Troy, MI (US); Guangzhao Mao, Northville, MI (US); Yanhua Zhang, Livonia, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 48 days.

(21) Appl. No.: 14/534,994

(22) Filed: Nov. 6, 2014

(65) Prior Publication Data

US 2015/0125926 A1 May 7, 2015

Related U.S. Application Data

(60) Provisional application No. 61/900,564, filed on Nov. 6, 2013.

(51) Int. Cl.
| | | |
|---|---|---|
| *A61K 47/02* | (2006.01) | |
| *A61K 47/48* | (2006.01) | |
| *A61K 31/522* | (2006.01) | |
| *B82Y 5/00* | (2011.01) | |

(52) U.S. Cl.
CPC ............ *A61K 47/02* (2013.01); *A61K 31/522* (2013.01); *A61K 47/48246* (2013.01); *A61K 47/48261* (2013.01); *A61K 47/48861* (2013.01); *B82Y 5/00* (2013.01); *Y10S 977/775* (2013.01); *Y10S 977/906* (2013.01); *Y10T 428/2982* (2015.01)

(58) Field of Classification Search
None
See application file for complete search history.

(56) References Cited

U.S. PATENT DOCUMENTS

| | | |
|---|---|---|
| 6,562,318 B1 | 5/2003 | Filler |
| 2002/0115598 A1 | 8/2002 | Muller et al. |
| 2011/0077204 A1 | 3/2011 | Kuchiiwa et al. |
| 2011/0144163 A1 | 6/2011 | Kingston et al. |
| 2012/0277283 A1 | 11/2012 | Mirkin et al. |
| 2013/0138032 A1 | 5/2013 | Kim et al. |

OTHER PUBLICATIONS

D. Menetrey, entitled "Retrograde tracing of neural pathways with a protein-gold complex", Histochemistry 1985, vol. 83, Issue 5, pp. 391-395, Department of Physiology, University of North Carolina, Chapel Hill, NC.
Fernanda Sousa, et al.,Journal entitled "Functionalized gold nanoparticles: a detailed in vivo multimodal microscopic brain distribution study". Nanoscale journal, 2010, 2, pp. 2826-2834, Copyright—The Royal Society of Chemistry 2010.
Massimo Masserini, Article entitled "Nanoparticles for Brain Drug Delivery", pp. 1-18, Hindawi Publishing Corp., ISRN Biochemistry, vol. 2013, Article ID 238428, 18 pages—Dept. of health Sciences, University of Milano-Bicocca, Monza, Italy.
Dale E. Moreno, et al., entitled "Identification of the Axon Pathways which Mediate Functional Recovery of a Paralyzed Hemidiaphragm following spinal Cord Hemisection in the Adult Rat", Department of Anatomy and Cell Biology, Wayne State University, School of Medicine, Detroit, MI. Experimental Neurology 116, pp. 219-228 (1992), Copyright 1992 by Academic Press, Inc.

*Primary Examiner* — Anand Desai
(74) *Attorney, Agent, or Firm* — Brinks Gilson & Lione

(57) ABSTRACT

A tripartite nanodevice comprising a targeting portion, a carrier portion, and at least one molecule to be delivered is provided. In particular, a gold nanoparticle linked to a targeting protein and capable of delivering a stimulant for the treatment of respiratory or disease is described. A method of making and a method of using a device of this nature are also described.

20 Claims, 6 Drawing Sheets

TRANSPORTER PROTEIN-COUPLED NANODEVICES FOR TARGETED DRUG DELIVERY

CROSS-REFERENCE TO RELATED APPLICATIONS

This application claims the benefit of U.S. Provisional Application Ser. No. 61/900,564 filed on Nov. 6, 2013, entitled "TRANSPORTER PROTEIN-COUPLED NANODEVICES FOR TARGETED DRUG DELIVERY," the entire contents of which are incorporated herein by reference.

BACKGROUND

The present invention relates to nanodevices. More particularly, the invention relates to a nanodevice incorporating a targeting protein which delivers a drug to a predetermined destination.

Out of convenience, many small molecule drugs are administered systemically, generally orally or by injection into the circulatory system. Both of these methods have disadvantages. In the case of oral administration, the drug must be able to remain intact in the highly acidic environment of the stomach (or metabolized from its administered form to its active form), then be absorbed into the bloodstream and circulate until it reaches its target. Injection removes the concerns associated with the digestive system but still requires a large dose that is given in a nonspecific fashion. As a result of these large doses, drug receptors in cells and tissues that are not the intended target for treatment are exposed to the drug, frequently causing undesired side effects. For instance, an inhibitor of mitosis that is administered systemically in order to minimize tumor growth will also inhibit mitosis in healthy cells which are replicating.

One condition which would particularly benefit from targeted drug treatment is cervical spinal cord injury. When injury occurs rostral to the phrenic nucleus, the descending bulbospinal respiratory pathways can become disrupted and the result can be a life-threatening weakness of respiratory muscle function, leading to increased deaths in this patient population from pneumonia, pulmonary emboli, and septicemia. These mortality factors may be caused directly by the weakening of the respiratory muscles after SCI or indirectly by the need to place patients on long-term mechanical ventilator support. Cervical spinal cord injury (SCI) patients dependent on ventilators experience respiratory system complications which are a major cause of re-hospitalization and death. Increasing respiratory output with pharmaceutical intervention could eliminate ventilator dependence and reduce respiratory complications.

The primary descending respiratory drive, provided by the bulbospinal pathway, transmits an excitatory impulse from the rostral ventral respiratory groups (rVRGs) in the medulla to the phrenic nuclei (PN) in the cervical spinal cord (C3-C6). The phrenic nuclei then stimulate the diaphragm muscle via the phrenic nerves resulting in contraction of the diaphragm to take a breath. Following a hemisection at the second cervical segment (C2Hx) the ipsilateral hemidiaphragm is paralyzed due to the disruption of the rVRG axons descending to the ipsilateral PN. The inability of the ipsilateral hemidiaphragm to contract results in respiratory stress and can lead to many related maladies over time. However, the crossed phrenic pathway, functionally latent in non-injured individuals, decussates caudal to the hemisection. Pharmaceutical intervention such as systemically administered theophylline can stimulate the cross phrenic pathway and restore function to the hemidiaphragm. Unfortunately in humans systemically administered theophylline at a therapeutic dose produces many unwanted side effects. In order to eliminate the side effects of theophylline while still maintaining the ability to stimulate the crossed phrenic pathway, theophylline will be bound to a nanoconjugate to selectively target only those neurons in the respiratory motor pathway. Injection of the nanoconjugate into the paralyzed hemidiaphragm immediately after a C2Hx will induce functional recovery of the diaphragm in the acute C2Hx injury model.

One class of drug that is used to treat the respiratory system is methylxanthines. These drugs are thought to assist with respiration by causing smooth muscle to dilate, thereby allowing constricted airways to open. The drugs have also been shown to induce recovery of diaphragm muscle paralyzed by spinal cord injury in both animals and humans. Among the drugs of this class are theophylline (THP), dyphylline, and aminophylline. Although effective, these drugs can also cause side effects such as nausea, chest pain, irregular heartbeat, and light headedness when delivered in such a way that they act systemically. In spinal cord injured patients, they can also cause insomnia and excessive nervousness. Because of these effects, the patients often cannot tolerate systemic drug therapy.

It has been a challenge to develop methods of and vehicles for delivering drugs to specific areas in the body.

SUMMARY

This disclosure relates to a tripartite nanodevice comprising a targeting portion, a carrier portion, and at least one molecule to be delivered to a patient.

In another embodiment, the invention provides a method of making a tripartite nanodevice comprising a targeting protein, a carrier portion, and at least one molecule to be delivered to a patient.

In another aspect, the invention comprises a method of using a tripartite nanodevice comprising a targeting protein, a carrier portion, and at least one molecule to be delivered to a patient.

Further objects, features, and advantages of the present invention will become apparent from consideration of the following description and the appended claims when taken in connection with the accompanying drawings.

DETAILED DESCRIPTION

The present invention generally provides a tripartite nanodevice comprising a targeting portion, a carrier portion, and at least one molecule to be delivered. In another aspect, it provides a method of making such a device. In another aspect, it provides a method of using such a device in a medical procedure.

The terms "substantially" or "about" used herein with reference to a quantity includes variations in the recited quantity that are equivalent to the quantity recited, such as an amount that is equivalent to the quantity recited for an intended purpose or function.

As used herein, "variant" refers to an amino acid sequence which is of the wild type or which has been altered by substitution, insertion, cross-over, deletion, and/or other genetic operation. For purposes of the present disclosure, a variant is not limited to a particular method by which it is generated. In some embodiments, a variant sequence can have increased, decreased, or substantially similar activities or properties in comparison to the parental sequence. In some embodiments, the polypeptide may contain one or more amino acid residues that have been mutated as compared to the amino acid sequence of the wild type polypeptide. In some embodiments, one or more amino acid residues of the polypeptide can be held constant, invariant, or not substituted as compared to a parent polypeptide in the variant polypeptides making up the plurality. In some embodiments, the parent polypeptide is used as the basis for generating variants with improved robustness or other properties. Variants can also differ in at least one of secondary structure, tertiary structure, and degree of foldedness As used herein, "derivative" refers to a chemically or biologically modified version of a chemical compound that is structurally similar to a parent compound and (actually or theoretically) derivable from that parent compound. A derivative mayor may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group) that do not substantially alter the function of the molecule for a desired purpose. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analogue" refers to a chemical compound that is structurally similar to another but differs slightly in composition (as in the replacement of one atom by an atom of a different element or in the presence of a particular functional group), but may or may not be derivable from the parent compound. A derivative differs from an analogue in that a parent compound may be the starting material to generate a derivative, whereas the parent compound may not necessarily be used as the starting material to generate an analogue.

As used herein, "nanodevice" or "nanoconjugate" refers to a structure from about 1 nanometer to about 1000 nanometers in one dimension, more preferably between about 2 nanometers and about 100 nanometers.

Figure 1:
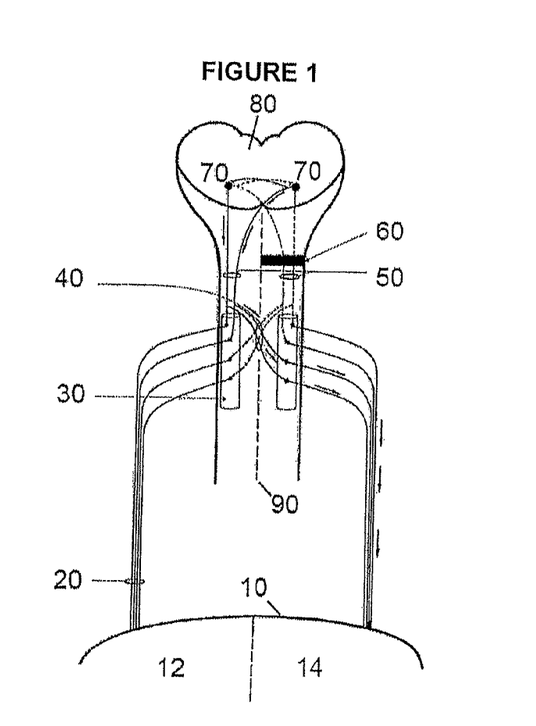
FIG. 1 is a diagram of selected portions of the mammalian central nervous system, the phrenic motor neurons, and the diaphragm muscle.

The descending bulbospinal respiratory pathways project from the rostral ventral respiratory group (rVRG) of neurons in the medulla to phrenic motoneurons located at the mid-cervical level of the spinal cord. Spinal cord injury rostral to the level of the phrenic nucleus may interrupt these descending respiratory axon pathways (FIG. 1). Since these axons provide the descending respiratory drive (excitation) to the phrenic motoneurons, interruption of the pathway leads to paralysis of the diaphragm.

Spinal cord hemisection at the second cervical level can disrupt the major descending respiratory pathways to the ipsilateral phrenic motoneurons and thus can paralyze the ipsilateral hemidiaphragm. Respiratory function can be restored to the paralyzed hemidiaphragm by activating a latent respiratory motor pathway which arises bilaterally from the rVRG, descends into the spinal cord contralateral to the injury and then crosses the spinal cord midline below the level of injury before innervating phrenic motoneurons ipsilateral to the injury. This latent pathway is referred to as the "crossed phrenic pathway" and recovery of the paralyzed hemidiaphragm mediated by the crossed phrenic pathway has been referred to as the "crossed phrenic phenomenon." Inspiratory drive to phrenic motoneurons is mediated by neurons in the rostral division of the ventral respiratory group (rVRG). These neurons project bilaterally to the phrenic nuclei and we have shown that both the crossed and uncrossed descending bulbospinal pathways have spinal decussating collaterals that project to both phrenic nuclei in adult rats. Hemisection rostral to the phrenic nucleus interrupts the descending pathways which results in paralysis of the ipsilateral hemidiaphragm.

The crossed phrenic pathway can be activated either by increasing respiratory drive, for example by cutting the phrenic nerve contralateral to hemisection to induce asphyxia, or by an acute or single administration of a variety of chemical compounds such as serotonin receptor agonists, NMDA receptor antagonists, theophylline, phosphodiesterase inhibitors and adenosine receptor antagonists. These drugs activate the latent respiratory pathway transiently; that is, when the effects of drug administration wear off, the crossed phrenic pathway reverts back to its latent state and the hemidiaphragm once again becomes paralyzed. The crossed phrenic pathway can restore phasic function to ipsilateral phrenic nerve by stimulation with pharmaceutical compounds.

Chronic administrations of theophylline, however, induce plasticity in the respiratory pathways which results in recovery that persists for days. Specifically, three days of orally administered theophylline three times per day (for a total of nine doses) was sufficient to bring about and maintain respiratory recovery that persisted for about 3 days, about 7 days, about 12 days, and about 30 days after the last drug administration in separate groups of animals. This suggests that chronic administration of theophylline induces functionally appropriate plasticity in the respiratory circuitry which in turn enables animals to achieve long term recovery of paralyzed hemidiaphragm motor function after a relatively short period of intervention.

Long term recovery can also be induced by using select drugs with specific actions, such as rolipram, a phosphodiesterase 4-specific inhibitor; pentoxifylline, a general phosphodiesterase inhibitor; and 1,3-dipropyl-8-cyclopentylxanthine (DPCPX), an adenosine A1 receptor antagonist. Theophylline is both a generalized phosphodiesterase inhibitor and an adenosine receptor antagonist. The underlying mechanisms for the theophylline-induced persistent recovery can be upregulation of cyclic AMP (cAMP) and activation of the protein kinase A (PKA) intracellular cascade.

Theophylline has been used clinically to treat respiratory problems such as asthma and chronic obstructive pulmonary disease in humans. Case studies that have assessed the effects of acute and chronic theophylline administration to patients with asymmetrical cervical spinal cord injury, acute respiratory failure, and ventilator dependence have produced positive outcomes.

In the case of the patient with spinal cord injury, both acute and chronically-administered theophylline increased neural activation to the diaphragm, especially on the more affected left side. Theophylline treatment was also associated with an increase in global central respiratory drive and inspiratory muscle force without changing expiratory airflows. Left diaphragm EMG activity was markedly increased following the administration of theophylline. Notably, upper parasternal intercostal EMG activity was also recruited on the left in spite of being below the level of cervical spinal cord injury.

In the case of the tetraplegic patient with acute respiratory failure and ventilator dependence, intravenous theophylline administered in increasing doses over the course of one day resulted in increased diaphragm EMG activity by a maximum of 50% at therapeutic levels of theophylline. Theophylline therapy enabled the patient to be weaned from ventilator support and discharged from the hospital.

Although the effects of theophylline on enhancing respiratory muscle strength have been documented, the drug when administered systemically is accompanied by undesirable side effects. In one study, more than 50% (14 of 24) of patients enrolled dropped out of the study primarily because they could not tolerate the levels of theophylline taken. The most common complaints were nausea and vomiting, nervousness (a "jittery feeling") and insomnia.

Theophylline is both an adenosine receptor antagonist and a phosphodiesterase (PDE) inhibitor. Chronic administration of rolipram (a PDE-4 specific inhibitor), pentoxifylline (a general PDE inhibitor), or DPCPX (an adenosine A1 receptor antagonist) also induce persistent functional recovery of a paralyzed hemidiaphragm in rat spinal cord injury model animals for as long as 10 days, the longest interval studied, after the animal is last exposed to the drugs. Although rolipram and pentoxifylline have been approved for clinical use, these "first generation" PDE inhibitors can induce the same side effects as theophylline, including nausea and vomiting.

"Second generation" PDE inhibitors such as roflumilast and cilomilast have been developed and have been tested in phase III clinical trials in Europe for their effectiveness as anti-inflammatory agents in treating chronic obstructive pulmonary disease (COPD). Although early reports have suggested reduced side effects compared to first generation inhibitors such as rolipram, Phase III efficacy studies in COPD involving both cilomilast and roflumilast have been hampered by a low therapeutic ratio. As the dose is increased to reach therapeutic levels, side effects also increase with the most common being nausea, diarrhea, abdominal pain, vomiting and dyspepsia. "Third generation" inhibitors are being pursued with the goal of maximizing therapeutic efficacy and further decreasing adverse effects although the synthesis and testing of these drugs are in very early phases at present.

Therefore, administration of theophylline or other xanthine derivatives in doses high enough to elicit a therapeutic effect but low enough to avoid or minimize side effects is desirable. Systemic administration of the drug leads to a concentration of drug within the body that is too high for many patients to tolerate due to side effects that occur at least partially because cells and tissues of the body that are not the intended therapeutic targets of the xanthine derivative drugs are contacted by the drugs and an undesired physiological response is elicited.

One possible application of this invention is to target the lower motor (phrenic) and pre-motor (rVRG) neurons responsible for diaphragmatic function. However, other neurons which drive other muscles or muscle groups, or other sets of cells or tissues which are susceptible to targeting are also envisioned as being encompassed by this invention.

In one embodiment, the invention of the present disclosure provides a nanodevice for targeted delivery of a drug. The nanodevice comprises a targeting portion and at least one molecule to be delivered. The nanodevice also optionally comprises a connecting portion.

The targeting portion is a portion of the nanodevice that provides the means of targeting the nanodevice to its destination in the body. The targeting portion may be a biological or chemical molecule including but not limited to a protein, a nucleic acid, a polysaccharide, a peptide, a lipid, a liposome, or a combination of any of these. In one embodiment, the targeting portion is a protein. In this embodiment the targeting portion is a chimera of wheat germ agglutinin (WGA) and horseradish peroxidase (HRP) variants. In an alternative embodiment, the protein could be, for example, an immunoglobulin or a different signalling protein. The protein variant may be isolated and purified natively or recombinantly.

One commercially available WGA-HRP conjugate comprises a 3-maleimidobenzoic acid N-hydroxysuccinimide ester linkage. Other linkages that allow for proper targeting can also be used. The WGA-HRP can be provided in solution, lyophilized in a powder, or in another liquid or solid format.

Lectins are carbohydrate-binding proteins which are found in a number of organisms. WGA is a plant lectin that preferentially binds to small molecules such as N-acetyl-D-glucosamine and sialic acid. WGA generally exists as part of a heterodimer of approximately 38 kilodaltons. HRP is a 44.2 kilodalton heme-binding oxoreductase enzyme which is found in the horseradish plant, *Armoracia rusticana*. HRP is useful in labelling neurons.

WGA (or a portion thereof, or portions of other plant lectins) can be conjugated N-terminal to or C-terminal to HRP for the purposes of this invention. There may also optionally be a linker region comprising a polypeptide disposed between the WGA and the HRP domains. This linker can be one or more amino acid residues and serves the purpose of separating the two domains functionally. Additionally, either WGA or HRP or both can optionally be variant proteins with at least one amino acid residue deleted from, added to, or substituted in the wild type sequence.

WGA-HRP can be taken up by the terminals of phrenic axons when injected into diaphragm muscle and retrogradely transported to phrenic motor neurons. In the case of an acute (lasting about 24 hours to about 48 hours) spinal cord injury, the WGA-HRP is further transported transsynaptically across physiologically active synapses to neurons in the rVRG and does not transport to any other neuron center other than the phrenic nucleus and rVRG. A similar but distinct phenomenon can be observed in the case of when the targeting portion comprises WGA conjugated to a fluorochrome, such as Alexa 488. In this case a plurality of neurons are labeled, which may reflect a more generalized excitability in the medulla upon chronic injury. These facts notwithstanding, in both acutely and chronically injured spinal cords, transport of WGA conjugates is seen specifically into neurons. For this reason one embodiment of this invention envisions using a WGA-HRP conjugate as the targeting portion of the nanodevice.

In another embodiment, HRP alone constitutes the targeting portion. HRP, even in the absence of WGA, is capable of being transported in a retrograde fashion through phrenic motor neurons. In another embodiment, WGA alone can constitute the targeting portion.

The connecting portion is conjugated to the targeting portion. The connecting portion can be primarily used as a scaffolding which is relatively inert in a chemical sense and which does not provoke a physiological response from the patient. In part, the connecting portion serves to carry the molecule to be delivered to the site of interest and facilitate its linkage to the targeting portion.

In one embodiment, the connecting portion may be a nanoparticle. Nanoparticles are also known as ultrafine particles and have a diameter of about 1 nanometer to about 100 nanometers, although fine particles sized with a diameter of about 100 to about 1000 nanometers may also be employed. The final portion of a nanodevice of tripartite construction is a molecule to be delivered.

Figure 2:
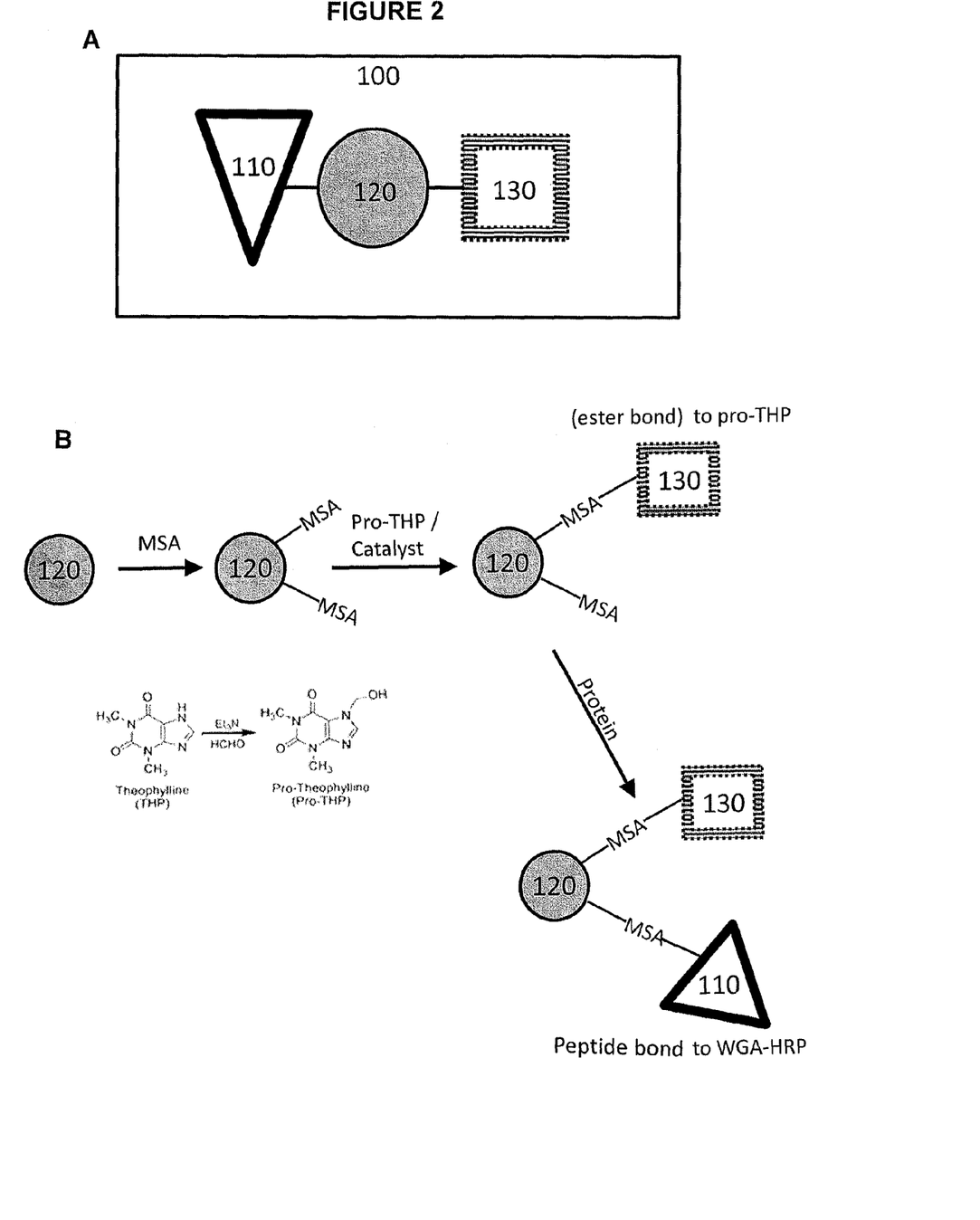
FIG. 2 is a diagram of the general synthesis scheme of the nanodevices of the present disclosure.

A general schematic representation for a tripartite nanodevice is illustrated in FIG. 2A. Here, linker 120 connects targeting portion 110 to molecule to be delivered 130, resulting in tripartite nanodevice 100. In one embodiment, targeting portion 110 is WGA-HRP, 120 is a gold nanoparticle, and 130 is a xanthine derivative.

FIG. 2B is a schematic illustration of the synthetic scheme described below.

One connecting portion that can be used in this invention is a gold nanoparticle. Gold (Au) nanoparticles (120 in FIG. 2B) have dimensions from about 1 nanometer to about 100 nanometers, or about 2 nanometers to about 75 nanometers, or about 3 nanometers to about 50 nanometers, or about 3 nanometers to about 25 nanometers, or about 3 nanometers to about 10 nanometers, or about 3.5 nanometers. Gold nanoparticles (GNPs) may be substantially spherical, or they may have other shapes, such as rods.

In one embodiment, gold nanoparticles are made by combining gold (III) chloride trihydrate with trisodium citrate and sodium borohydride. In one non-limiting example, the gold nanoparticles may be made in an aqueous solution. When the volume of the solution is about 500 milliliters (ml) in, for example, a 1 liter Erlenmeyer flask, the concentration of a gold chloride salt such as gold (III) chloride trihydrate is about 0.25 millimolar (mM) and trisodium citrate at a concentration of about 0.25 mM is added with vigorous stirring at about room temperature. About 15 ml of ice cold sodium borohydride at a concentration of about 100 mM is added to the solution. At this point, there should be a color change and the solution should become pink. Next, the pH of the solution is adjusted to about 11 by adding the appropriate amount of mercaptosuccinic acid (MSA) to effect the change (for instance, about 50 milligrams (mg)). Conducting the reaction at pH 11 can be advantageous in order to minimize or eliminate precipitation of MSA in the reaction. Stirring then continues for about 12 hours. The solution is then concentrated to about 2.5 mg/ml gold by ultracentrifugation using commercially available filtration devices. Ultracentrifugation, particularly in centrifuge tubes having a nominal molecular weight limit (NMWL) of about 10,000, assists in keeping gold nanoparticles dispersed, and unwanted additional chemicals (such as for example free MSA, catalysts, and other free molecules including drugs and prodrugs to be delivered) out of the final product. The particles are then washed multiple times with deionized water. Reaction with mercaptosuccinic acid provides functional groups on the GNP for binding to other molecules, both transporter portions and molecules to be delivered.

In another embodiment, the gold nanoparticles are formed using a protocol similar to that described above. In this alternative embodiment, an aqueous solution of sodium borohydride (about 25 ml at a concentration of about 200 mM) is slowly added to a reaction mixture of about 4 ml gold chloride salt at about 125 mM in deionized water and about 100 ml mercaptosuccinic acid at about 5 mM in an alcohol, such as methanol. Conducting the reaction at about pH 11 can be advantageous in order to minimize or eliminate precipitation of MSA in the reaction, thereby causing undesired aggregation in the water/alcohol mixture. The resulting mercaptosuccinic acid-GNP can then be centrifuged and washed in a water/alcohol mixture and vacuum dried into a powder.

Although GNPs 120 can be synthesized in aggregate, it can be advantageous to synthesize them in monodisperse format. Molecules to be delivered can be more efficiently bound to the surface of monodisperse gold nanoparticles, including those with a size about 3.5 nanometers. GNPs of this size are well-suited for predictable and stable release of the molecule to be delivered.

The nanoparticles 100 formed by the above protocols or other means of creating gold nanoparticles can be analyzed by Fourier transform infrared spectroscopy (FTIR), ultraviolet/visible spectrometry, transmission electron microscopy, atomic force microscopy, dynamic light scattering, or any other method suitable to analyzing nanoparticles.

In another embodiment, the connecting portion may comprise a polymer. The connecting portion may comprise a dendrimer. The connecting portion may also be a nanotube, such as a fullerene, a carbon nanotube, a silicon nanotube, a DNA nanotube, a boron nitride nanotube, or any inorganic nanotube, provided that these nanotubes are biocompatible. The connecting portion may also be other types of nanoparticles, such as iron oxide, silver, silicon, quantum dots, polymeric micelles, polymeric nanoparticles, liposomes, albumin, and combination of them in the form of multicomponent systems, imaging agents, and theranostics.

The nanoconjugate of the present disclosure harbors a number of advantages over existing technologies. First, the surface modifications described impart the ability to carry a number of different drugs or other molecules. Second, the conjugates have sufficient solubility and low aggregation which allow them to function in a patient and deliver their molecules. Third, no other known technology combines a targeting portion (such as a plant lectin), a linking portion (such as a gold nanoparticle), and a drug or drug precursor in order to achieve targeted delivery of an effective but low-dose quantity of drug to a specific portion of the body.

In another embodiment, the connection portion may comprise a biological molecule. In particular, a protein or a nucleic acid may be used. A protein used for this purpose must be minimally immunogenic in order to avoid an unintended reaction.

The nanodevice also comprises a molecule to be delivered. The molecule can be bound to the nanodevice by a breakable, such as a hydrolyzable or reducible covalent bond. The molecule can also be bound by physical bonds such as ionic and hydrogen bonds.

In one embodiment, the molecule to be delivered can be a small molecule. A particular class of small molecules that can be used are xanthine derivatives (130 in FIGS. 2A and 2B). Xanthine derivatives are used as mild stimulants and bronchodilators, especially in the treatment of asthma and other respiratory diseases. Xanthine derivatives function by opposing the actions of adenosine and keeping the central nervous system in a state of alertness. Therefore, any small molecule which is known to either oppose the actions of adenosine, or keep the central nervous system alert, or both, can be used in a nanodevice as disclosed herein.

A class of xanthine derivatives that is of particular significance is the methylxanthine class. Methylxanthines affect the airways and stimulate heart rate and force of contraction. Methylxanthines induce acid and pepsin secretions in the gastrointestinal tract. These molecules act as competitive nonselective phosphodiesterase inhibitors which act to raise intracellular cAMP, activate PKA, inhibit tumor necrosis factor alpha and leukotriene synthesis, and reduce inflammation and innate immunity in addition to their roles as adenosine receptor antagonists.

Methylxanthines include caffeine, aminophylline, IBMX (3-isobutyl-1-methylxanthine), paraxanthine, pentoxifylline, theobromine, and theophylline. The structures of methylxanthines can influence their specificity for different receptor types. For instance, IBMX inhibits a variety of phosphodiesterases, but does not inhibit PDE8 or PDE9. The nanodevice may contain at least one of these methylxanthines, or one or more methylxanthines not listed above.

In one embodiment, the molecule to be delivered comprises theophylline or a theophylline derivative, including salts thereof. It can be advantageous to deliver a molecule as a prodrug which is processed in the body after administration to release the active form of the drug. One such prodrug of theophylline which can be used in this invention is the acyl derivative 7-hydroxymethyl theophylline (pro-THP), which is simplest 7-additive pro-form theophylline for bioconjugation especially to form ester bond. Other prodrugs of theophylline can be employed, such as 7-hydroxyalkyl, 7-alkylcarboxylate pro-form theophylline, and 7-hydroxymethyl theophylline, which can further react with linker molecules to form biodegradable ester (see FIG. 2B), peptide or disulfide bonds.

Pro-THP is synthesized according to a known method. Theophylline is used as a starting material and is added in about a 1:1 mass ratio to 36% aqueous formaldehyde. For instance, about 2.6 g THP is added to about 2.6 g formaldehyde. Next, about 1.469 g triethylamine is added and the mixture is stirred vigorously. After the mixture becomes homogeneous, about 3 ml of tetrahydrofuran is added. The reaction can then be kept for recrystallization for about 2 days after the end of stirring. A white solid mass of pro-THP is formed.

In another embodiment, the molecule to be delivered comprises 1,3-dipropyl-8-cyclopentylxanthine (DPCPX) or a derivative, salt, or prodrug thereof. Because DPCPX is specifically an adenosine A1 receptor antagonist, as opposed to theophylline, which is an A1 and A2a adenosine receptor antagonist and a general PDE inhibitor, it is possible that DPCPX may be yield more effective therapeutic results at a lower dose than theophylline. DPCPX is provided as a prodrug, which can be prepared in a similar manner to the preparation of pro-THP described above or in another way.

Other embodiments of this invention will use combinations of at least two of pro-THP, DPCPX, other xanthine derivatives, and other small molecules that are beneficial in providing therapeutic results. These drugs can be provided in defined ratios.

The three components of the nanodevice (targeting portion, connecting portion, and molecule to be delivered) are bound or linked together to comprise a single device. The targeting portion can be first linked to the connecting portion, then the connecting portion bonded to the molecule to be delivered, or the molecule can be bonded to the connecting portion first, followed by binding to the targeting portion.

The molecule to be delivered is also bound to the connecting portion. In one embodiment, a "fast drug release" linker between the connecting portion and the molecule to be delivered may be employed. In another embodiment, a "slow drug release" linker may be used. In yet another embodiment, a combination of fast drug release and slow drug release linkers may be used in a predetermined ratio.

In an embodiment where a slow drug release linker is employed, the linker can be an ester linker. One way of forming an ester bond is to first suspend the gold nanoparticles at a concentration of about 5 milligrams per milliliter in a solution of about 100 mM 2-(N-morpholino)ethanesulfonic acid (MES) buffer. The pH of this mixture is optimally about 4.7. In a mixture of about 5 ml of GNPs, about 5.2 mg of pro-theophylline and about 5 ml of dimethyl sulfoxide (DMSO) are added, along with about 4.8 mg of EDC and about 1.7 mg of 4-dimethylaminopyiridine (DMAP) used as a catalyst. The reaction is allowed to continue for about 48 hours and the product is then washed multiple times with deionized water and concentrated.

In other embodiments, different buffers, such as acetate buffers, may be used, but it can be advantageous to use MES as this buffer ensures that ester bond formation only occurs on the surface of the GNPs. For example, acetate buffers may result in pro-THP reacting with free acetate rather than the GNP.

In another embodiment, the linker can be an amide bond (see FIG. 2B). In yet another embodiment, ester linkers and amide bonds can be combined. Amine bonds release approximately half of the amount of drug molecules as do ester linkers. Ester linkers can be broken down by esterase action.

Figure 5:
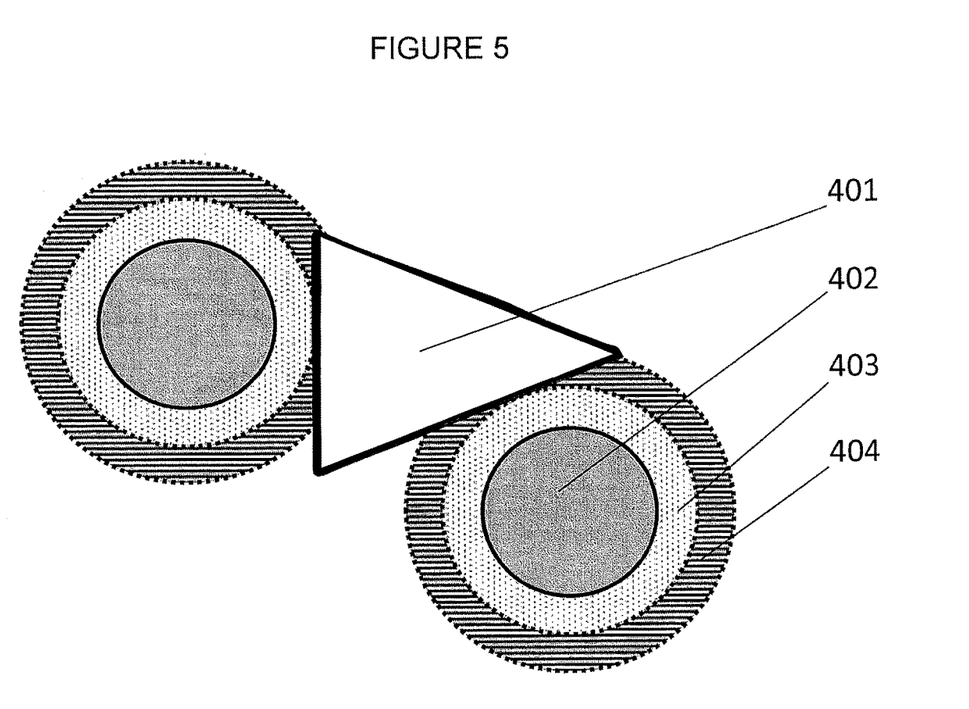
FIG. 5 is a schematic illustration of a tripartite nanodevice in accordance with one embodiment of the present invention.

A schematic example of a tripartite nanodevice generated by the above scheme is illustrated in FIG. 5. In this illustration, one unit of the protein WGA-HRP 401 bridges two gold nanoparticles 402. The GNPs 402 have been coated with MSA and are bound by a surrounding layer of pro-THP. It will thus be appreciated how all or nearly all of the surface of a GNP 402 can be coated with a plurality of drug molecules to be delivered.

It will be appreciated by those having skill in the art that the amounts of protein, drug, and linker, as well as any catalysts and buffers, can be adjusted by a person synthesizing a nanodevice in order to result in desired ratios between protein, drug, and linker, for different uses of the invention.

In an embodiment where a fast drug release linker is used, the linker can be a disulfide linker. pro-THP can be reacted with succinic anhydride in the presence of dimethylformamide/dimethylacetamide in basic conditions. The acid functional groups of the intermediate are activated using N-hydroxysuccinimide (NHS) and N,N'-dicyclohexylcarbodiimide as activating agents and triethylamine as a base in DMSO. The dicyclohexylurea generated during the reaction precipitates, and can be removed by filtration. The reaction mixture can be freeze dried to produce an NHS ester-activated theophylline derivative. The product is further reacted with 2-aminoethanethiol under basic conditions in DMSO to produce a reactive thiol group.

The carboxylic groups on the surface of gold nanoparticles are then activated using benzotriazol-1-yl-oxytripyrrolidinophosphonium hexafluorophosphate (PyBOP) as activating agent, diethyl isopropyl amine as a base in DMSO. After 1 hour of stirring, 2-(2-(pyridinyl)disulfanyl) ethanamine is added to the reaction mixture and kept stirring for 2 days to finish the reaction at room temperature. The final product is purified using ultracentrifugation. The conjugation of the drug/gold nanoparticle to WGA-HRP is unchanged.

In some embodiments, a combination of fast drug release and slow drug release linkers can be used. When this is the case, the patient can receive an initial dose of the drug when the fast drug release linkers are broken, and continue to receive drugs from the nanodevices having slow drug release linkers.

In an embodiment where the targeting portion comprises WGA-HRP and the connecting portion comprises a gold nanoparticle coated with mercaptosuccinic acid and bound to a molecule to be delivered, such as pro-THP, the WGA-HRP can be attached to the GNP-pro-THP by a peptide bond. Enhanced results are particularly seen when the GNP-pro-THP is cooled to 4 degrees Celsius and diluted to a volume of about 20 ml with deionized water which is also at 4 degrees. Then, about 5 mg of WGA-HRP is combined with about 20 mg 1-ethyl-3-(3-dimethylaminopropyl)carbodiimide (EDC) and about 6 mg N-hydroxysuccinimide as a catalyst. The reaction is allowed to proceed preferably for about 30 minutes and can then be washed in deionized water and concentrated for use. It can be advantageous to use NHS rather than similar compounds such as, for instance, hydroxybenzotriazole. The amounts of NHS and EDC are highly optimized to minimize over-crosslinking of GNP to protein and therefore aggregation of the final product. These steps comprise a preferred embodiment of the invention.

In another aspect, this invention refers to the administration of a nanodevice to enhance respiratory function in a patient with an injury of the central nervous system. The following example provided hereafter is merely exemplary and does not provide for the exclusion of other doses or administration regimens that may provide good therapeutic outcomes.

In one case, rats with hemisection at C2Hx, hereafter "C2Hx rats," have undergone surgical treatment to disrupt the bulbospinal pathway from the rVRG to the PN, the primary source for descending respiratory drive. Paralysis of the ipsilateral diaphragm muscle in C2Hx confirmed by electomygram (EMG). In such rats, the latent crossed phrenic pathway remains intact, as axons decussate caudal to injury.

In one example, a nanodevice with a targeting portion of WGA-HRP and a molecule to be delivered of pro-THP, the pro-THP being bound to the connecting portion by a slow drug release linker, was administered by injection into the paralyzed hemidiaphragms of a cohort of 11 C2-hemisected rats. About 50 µl of the nanodevice, which contained about 0.275 µg of pro-THP, was injected. Five 10 µl injections were conducted at even spatial intervals to spread the conjugate throughout the hemidiaphragm. This constitutes a single round of injections and thus considered to be a one-time, single-injection type of treatment.

The inventive tripartite nanodevice comprising theophylline coupled to WGA-HRP via a gold nanoparticle has been shown in C2Hx rats to reduce the amount of theophylline required to realize recovery from traumatic spine injury from levels of 15 mg/kg in a systemic treatment to just 0.07 mg/kg. Such a reduction would greatly reduce the undesirable side effects of systemic administration of high dosages of theophylline. Injection of the nanoconjugate into the diaphragm immediately after a C2 hemisection (acute injury) targets the phrenic motoneurons in the cervical spinal cord by retrograde transport followed by transsynaptic transport to the rVRG neurons in the medulla.

Figure 3:
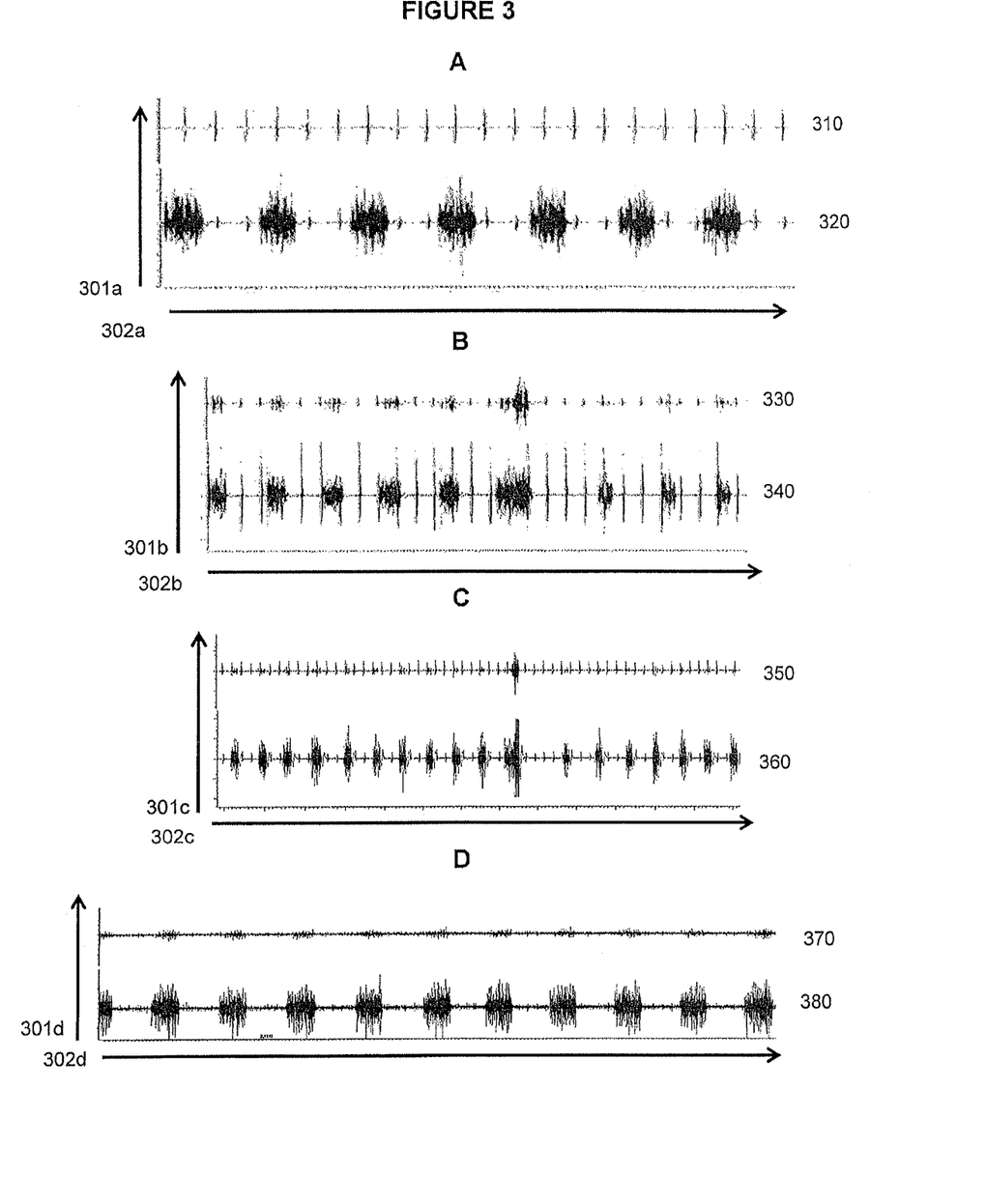
FIG. 3 is a series of experimental readouts in graphical form conducted on a rat model of spinal cord injury using a tripartite nanoconjugate in accordance with one embodiment of the present disclosure.

FIG. 3 illustrates a trial of C2Hx rats that have been treated with a WGA-HRP/gold/pro-theophylline nanodevice. In each plot, the Y-axis 301*a/b/c/d* represents a voltage signal and the X-axis 302*a/b/c/d* represents time, increasing from left to right. Two different types of plots are shown in FIG. 3; FIG. 3A-C are EMG recordings and FIG. 3D is a phrenic nerve recording.

FIG. 3A shows an EMG from a C2Hx rat immediately after surgery. This injury causes immediate paralysis of the ipsilateral hemidiaphragm as seen by the lack of signal demonstrated in plot 310. Plot 320 shows that the contralateral hemidiaphragm continues to have normal phasic function.

Turning to FIG. 3B, two days after nanoconjugate injection with a 0.07 mg/kg dose of pro-THP, phasic muscle function has already returned to the ipsilateral hemidiaphragm (trace 330.) In some cases, 80% of the amount of activity of the uninjured hemidiaphragm has been observed. The contralateral hemidiaphragm has normal phasic function (trace 340.)

FIG. 3C shows the same animal fourteen days post-injection with the nanodevice. In trace 350, a phasic, though reduced when compared to trace 330, response in the ipsilateral hemidiaphragm can be observed. Trace 360 continues to show normal function. Thus, in view of FIGS. 3B and 3C, restored diaphragm function can be detected as early as 2 days post-injection and persisting until at least 14 days thereafter (the longest post-injection time tested thus far). Such a result is remarkable not only for the persistence and the low dosage of drug, but also for the fact that it can be achieved with a single injection, and up to about 80% of function can be recovered.

Finally, FIG. 3D is a phrenic nerve recording taken seven days post-injection. Trace 370 shows that ipsilateral phrenic nerve signal has phasic function, and is actually synchronized with the signal from the contralateral phrenic nerve (trace 380). This direct measure from the phrenic nerves confirms bulbospinal pathway function.

Studies like those shown in FIG. 3A-D were conducted with DPCPX. The dosage required for recovery in a rat were a remarkably low 0.093 microgram single administration. Therefore, even as excellent as pro-THP has proven to be, DPCPX might be even greater.

The most effective dosages of the nanoconjugate are not apparent prior to trial administrations. For instance, in the study outlined in FIG. 3, the optimal drug dose was found to be 0.07 mg/kg pro-theophylline. However, a dose of 0.03 mg/kg was found to induce minimal to no recovery in the ipsilateral diaphragm, and a slightly higher dose (0.12 mg/kg) was found to have an inhibitory effect resembling that of systemically-delivered theophylline. Thus, for any condition which a tripartite nanodevice of this type might be employed, specific dosing parameters must be identified.

Retrograde labeling in both the phrenic and rVRG was observed as early as at 3 days suggesting that the nanodevice was transported to the target neurons by this time, but the drug was not yet activated or released from the device to mediate its action on the target cells. The earliest time that recovery can be observed is about 3 days, and recovery extends for at least about 12 days, the longest time point tested to date. In some cases recovery is restricted to the posterior (crural) region of the diaphragm. EMG assessments of treated diaphragms (as shown by example in FIG. 4) detected recovery in all regions of the diaphragm examined (the anterior (sternal), lateral (costal) and posterior (crural) regions) from 7-12 days post injection. Bilateral WGA-HRP activity in the rVRG after conjugate nanodevice injection was observed. Recovery qualitatively appeared to increase from 7-10 days and then persisted out to 12 days. The terminal electrophysiological experiments proposed in each aim will give us a quantitative assessment of recovery along with the newly proposed plethysmography studies.

Qualitative EMG assessment of hemidiaphragm recovery suggested that the slow-drug release conjugate induces recovery between 6-12 days post injection while the fast-drug release conjugate induces recovery much sooner (between 2-16 days post injection.) Multiple systemic administrations of theophylline over 3 days can induce long-lasting recovery.

Figure 4:
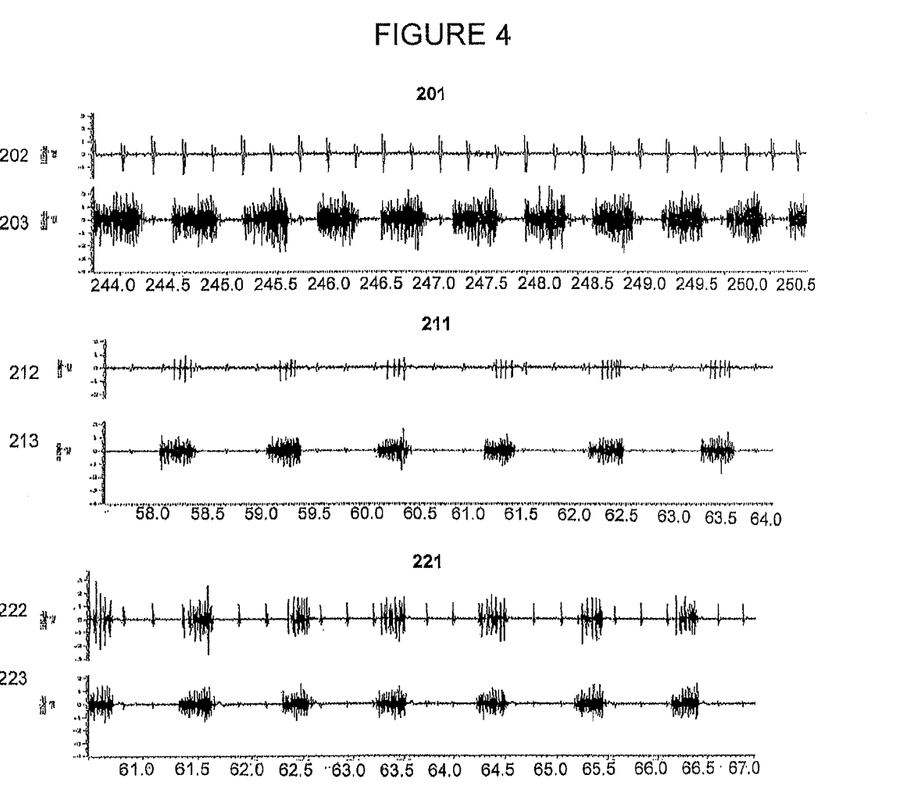
FIG. 4 is a series of electromyograms generated in experiments on animals, some of which were treated with nanodevices as described herein.

A non-limiting example of a trial of an embodiment of the invention of this disclosure is illustrated in FIG. 4. Shown are EMGs taken after hemisection of a spinal cord of a rat followed by treatment with a nanodevice having a targeting portion comprising WGA-HRP, a connecting portion comprising a gold nanoparticle, and a molecule to be delivered comprising proTHP. The injury by hemisection was made on the left side of the spinal cord and the nanodevice was injected into the left, paralyzed hemidiaphragm. EMG 201 was measured two days post-injection and shows normal activity on the right, uninjured side of the diaphragm in plot 203. However, in plot 202, the injured left side shows only small spikes which are simply electrocardiograms (EKGs) from the heart of the animal.

EMG 211 was measured on the same animal four days post-injection. A small level of recovery is seen on the left, injured side in plot 212.

EMG 221 was measured on the same animal ten days post-injection. Plot 222 illustrates that there is substantial recovery in the left, injured side of the diaphragm, whereas plot 223 can be used as a baseline comparison. However, as is known in the field, EMG readouts can only be qualitatively compared. This experiment, which is non-limiting in nature, serves to show that a single injection of a nanodevice exemplary of the present disclosure can be used to treat a paralyzed diaphragm.

A single injection of the slow-drug release, the fast-drug release or a combination of both conjugates may induce long-lasting recovery as well.

Tripartite nanodevices of this format are envisioned for use in treatment of paralyzed muscles besides the diaphragm. For example, in certain muscle groups, a growth factor such as brain-derived neurotrophic factor (BDNF) can be substituted as the delivered drug. Importantly, each of the three components of the nanodevice can be altered to achieve the desired effect.

Although a tripartite nanodevice of this type is envisioned to be used in a patient suffering from a traumatic spinal cord injury (SCI), either acute or chronic, there are other conditions which may benefit from such a targeted and specific approach. These conditions include, but are not limited to, central cord syndrome, Brown-Sequard syndrome, anterior cord syndrome, amyotrophic lateral sclerosis (ALS), multiple sclerosis, stroke, Alzheimer's disease, Parkinson's disease, Huntington's disease, transverse myelitis, paraplegia, tetraplegia, polio, autonomic dysreflexia, and congenital disorders affecting the spine and nervous system including muscular dystrophy.

Further, a chronically-injured patient may have an overactive central nervous system. Such hyperactivity can be observed as hyperactivity of neurons below the level of the injury as well as above the injury in the brainstem. Hyperactivity may activate initial latent uninjured pathways to induce a minimal amount of spontaneous recovery of the muscles in lieu of regeneration of injured pathways. A patient with such a condition may benefit from suppression of overactivity of the respiratory pathway such as might be offered by treatment with a sedative. Drugs with such sedative effects include Baclofen and 2-chloro-N-6-cyclopentyladenosine, among others. Combination therapy with the nanodevice of the present disclosure may be achieved by inclusion of the sedative drug on the nanodevice. In another embodiment, the sedative might be administered systemically prior to administration of a stimulant-carrying nanodevice (such as one carrying DCPCX or pro-theophylline.)

In a first reduced to practice embodiment, a tripartite nanoconjugate in accordance with the present invention was synthesized. THP was converted to its prodrug form pro-THP using the Mannich reaction in order to conjugate the drug to the mercaptosuccinic acid-capped gold nanoparticle (MSA-GNP) with an ester bond linkage. Such an ester bond is hydrolysable and is used to release the drug in physiological conditions from its nanoparticle carrier. THP was added in a 1:1 weight ratio to formaldehyde (36% in water); that is, 2.6 g THP was added to 2.6 g formaldehyde followed by the addition of 1.5 g triethylamine with vigorous stirring. After the mixture became homogeneous, 3 ml of tetrahydrofuran was added. The reaction proceeded for 2 days in quiescent conditions to allow crystallization of pro-THP. The crystal then was filtered and washed using deionized water. The final white powder was 2.16 g (71% yield).

Thereafter, MSA-GNP was synthesized. A 500 ml aqueous solution containing 0.25 mM $HAuCl_4.3H_2O$ and 0.25 mM trisodium citrate was prepared in an Erlenmeyer flask under vigorous stirring at room temperature. A 15 ml of ice cold 0.1 M $NaBH_4$ solution was added to the solution and the solution color changed to pink immediately signalling the GNP formation. After adjusting the pH of the solution to 11 with 0.1 M NaOH solution, 50 mg MSA was added and the solution was stirred for 12 h. The final solution was concentrated to 2.5 g (gold)/l by ultracentrifugation using 10000 MW Millipore Amicon® centrifuging units and washed by deionized water several times. UV-vis, tunneling electron microscopy (TEM), and dynamic light scattering (DLS) were employed to measuring the size of the intermediate and final products of the nanoconjugate.

MSA-GNP was concentrated to 5 mg (gold)/ml in 5 ml 0.1 M MES buffer. The pH value was adjusted to 4.7 using 0.1 M MES buffer to favor the ester bond formation. Acetic acid was not used here to adjust the pH but instead to prevent the esterification with the solvent. 5.2 mg pro-THP was added to 5 ml DMSO containing 4.8 mg EDC and 1.7 ml of DMAP according to the Steglish Reaction. After 40 h of the reaction, the product was purified by washing with deionized water and concentrated several times for the next conjugations step.

In order to conjugate WGA-HRP to pro-THP/MSA-GNP, the pro-THP/MSA-GNP solution diluted to 0.1 mg/ml drug concentration by deionized water was maintained at 4° C. for the reaction at pH ~6.6. 5 mg WGA-HRP, 20 mg EDC, and 6 mg NHS were added to the pro-THP/MSA-GNP solution. The reaction proceeded for 30 min followed by washing with deionized water with a final concentration of 0.4 g (pro-THP)/l in deionized water. The final solution can be stored at 4° C. for several months before animal injection. Freezing of the product should be avoided.

UV-vis absorption spectroscopy (Varian Cary 50) was employed to determine the GNP size based on the Beer-Lambert Law.

TEM images were taken by JEOL JEM-2010. Samples were prepared by placing a droplet of the GNP solution on a Formvar-coated copper TEM grid. Excess liquid was absorbed by a piece of filter paper under the grid and dried in air. The working condition of the TEM in the bright field was set 200 keV to capture the images.

Dynamic light scattering (DLS) and zeta potential were measured using a Malvern Nano-ZS. 1 ml the solution was transferred to a 2.0 mL polystyrene cuvette. The Z-average hydrodynamic diameter (HD), polydispersity index (PDI), and zeta potential were measured at 25° C. Before scanning, the solution was stabilized for 120 s and for each sample, 15 scans were performed to optimize the final signal.

Atomic force microscopy (AFM) was used to measure the nanoconjugate size. AFM imaging was conducted using a Dimension 3100 AFM from Bruker. Tapping mode in air and in water were conducted on mica. In order to image nanoconjugate particles with an overall negative charge, nanoparticle binding to negatively charged mica was enhanced by divalent metal ions. 20 microliters of $10^{-6}$ M $MnCl_2$ solution was placed on a 1×1 cm2 mica sheet and the substrate was dried after 10 s. Then 10 µl of 20 mg/L nanoconjugate solution was added, and the mica substrate was rinsed with deionized water and dried with nitrogen gas after 30 s. The AFM images were analyzed using Nanoscope software version 5.12b by VEECO. The sectional height image analysis command was employed to determine particle size. The lateral dimension of a particle was determined at the full-width at half-maximum height in order to minimize tip convolution.

To quantify the composition of the GNP-drug-protein nanodevice, thermal gravimetric analysis (TGA) was performed on the SDT-Q-600 instrument using air as working gas. The temperature range on the stage was from 100° C. to 800° C. with a heating speed 10° C./min.

Figure 6:
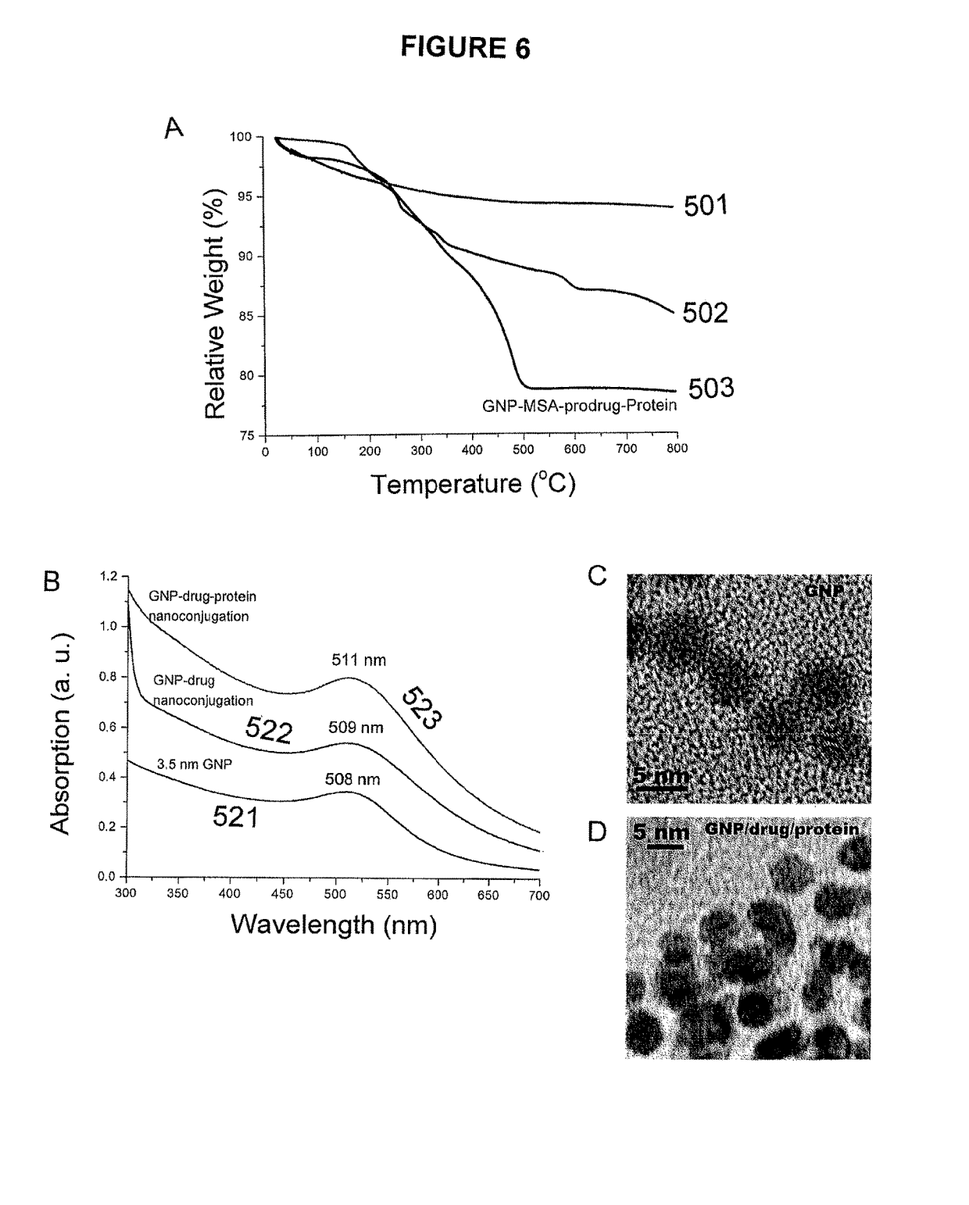
FIG. 6 shows plots and photographs which confirm the coating and treating of gold nanoparticles and the creation of tripartite nanodevices.

FIG. 6A shows TGA curves of MSA-GNP (501), pro-THP/MSA-GNP (502), and pro-THP/MSA-GNP/WGA-HRP (503) with respective weight loss of 6.15%, 15.0%, and 21.6% at 800° C. The weight loss was attributed to the burn-off of the organic species (MSA, pro-THP, and WGA-HRP) and was used to calculate their conjugated amount to the GNP. The GNP size was assumed to be 4 nm in diameter according to the TEM analysis, which is equivalent to 2,020 gold atoms and molecular weight of 390,000 g/M (particle). The weight lost of 6.15% for MSA-GNP corresponds to a surface coverage of 170 MSA molecules per GNP or 3.4/ $nm^2$. The weight loss of 15.0% for pro-THP/MSA-GNP (85% gold: 5.57% MSA: 9.42% pro-THP) corresponds to 204 pro-THP molecules per GNP. This is lower than the surface saturation of 340 pro-THP per GNP if all 170 MSA molecules have reacted with pro-THP. Then free MSA sites on GNP will be able to further react with the amine group of WGA-HRP to form the peptide bond. The peptide bond is stable in physiological conditions. The final step of 22.5% weight loss was used to calculate the final product chemical composition: 77.5% gold, 5.0% MSA, 8.6% pro-THP, and 8.9% WGA-HRP. This means that in this embodiment, 2 GNPs are bonded to one WGA-HRP molecule. In other embodiments wherein larger (about 15 nm) GNPs are used, the molecules observed tend to have only 1 GNP bonded to one WGA-HRP molecule. Thus, a person doing the synthesis can exercise control over this ratio.

Similarly, FIG. 6B shows UV-visible spectrometry data for the conjugate devices. The original absorption of MSA-GNP (plot 521) with a peak at 508 nm is consistent of GNP size range of 3-5 nm. There is only a slight peak wavelength shift to 509 nm (plot 522) after conjugation to pro-THP and to 511 nm after further conjugation to WGA-HRP (plot 523). This suggests that the GNP size is unchanged after conjugations to drugs and the protein and there is no aggregation of the GNPs after the conjugation reactions.

Finally, FIG. 6C-6D show TEM images of GNPs which either have or have not been treated with MSA and drug. In FIG. 6C, discrete GNPs of a smaller radius are visible. The GNP-drug-protein tripartite conjugate of FIG. 6D shows a final product size ranging from about 6.5 nm to about 15 nm in length, showing that in this embodiment two GNPs are linked through a single WGA-HRP. AFM data, not provided here, further confirmed these attributes of the particles.

In a second reduced to practice embodiment, a (WGA-HRP)-Au-(pro-THP) tripartite nanoconjugate in accordance with the principles of the present invention was injected 48 hours following C2Hx hemisection. Recovery of the diaphragm muscle was investigated using an EMG recording in C2Hx rats which had been treated with a delivered dose range of 0.03 mg/kg to 0.06 mg/kg (n=6 rats). Rats that received a 0.03 mg/kg dose demonstrated a minimal return of diaphragm muscle activity, if detectable at all, (n=5). The (WGA-HRP)-Au-(pro-THP) nanoconjugate, when injected immediately after the C2Hx procedure, demonstrated minimal recovery at doses ranging from 0.019 mg/kg to 0.048 mg/kg (n=8). A subset (n=2) showed no recovery when administered doses of 0.024 mg/kg and 0.049 m/kg. The (WGA-HRP)-Au-(pro-THP) nanoconjugate when injected immediately after the C2Hx n=15 demonstrates recovery at doses 0.06-0.07 mg/kg.

The (WGA-HRP)-Au-(pro-THP) nanoconjugate, when injected immediately after the C2Hx procedure, demonstrated a disruption in the contraction of the diaphragm at the dose of 0.12 mg/kg, suggesting over stimulation (n=2). The (WGA-HRP)-Au-(pro-THP) conjugate has been viewed in the spinal cord and medulla in 1 rat using a 3,3',5,5'-tetramethylbenzidine (TMB) reaction to visualize the HRP component. Significantly, three control animals that received injections of a gold-pro-THP bipartite conjugate showed no recovery of the diaphragm muscle (n=3, tested from day 2 to day 12), or at the level of the phrenic nerve (n=1 at 12 days). This illustrates that all three portions of the tripartite nanoconjugate must be present and linked in order to achieve optimal results.

In a third reduced to practice embodiment, the present invention comprising a (WGA-HRP)-Au-(DPCPX) tripartite nanoconjugate was tested at four different concentrations in C2Hx rats, measuring diaphragm function after the injury. The first pilot study tested the effect of 0.06 mg/kg dose of the tripartite nanoconjugate on the recovery of diaphragm function. No recovery was seen in 5 animals. The dose was then lowered significantly to 0.6-0.8 micrograms of nanoconjugate per kilogram and recovery was observed in 9 out of 12 animals. Control animals received (a) WGA-HRP+ gold bipartite nanoconjugate, or (b) gold+drug. In these animals, only minimal recovery could be detected in 1 out of 6 animals in each group (1 out of 6 in WGA-HRP+gold and 1 out of 6 in gold+drug group). A low dose of 0.2-0.4 micrograms/kg and high 1.0-1.2 micrograms/kg dose of the DPCPX nanoconjugate resulted in diaphragmatic recovery in 2 out of 7 and 4 out of 8 animals, respectively, using the electromyographic method.

While the present invention has been described in terms of certain preferred embodiments, it will be understood that the invention is not limited to the disclosed embodiments, as those having skill in the art may make various modifications without departing from the scope of the following claims.

The invention claimed is:

1. A tripartite nanodevice comprising:
   at least one targeting portion comprising a wheat germ agglutinin-horseradish peroxidase conjugate;
   at least one carrier portion comprising a gold nanoparticle having a diameter of about 1 nanometer to about 25 nanometers; and
   at least one small molecule to be delivered, the at least one small molecule comprising a xanthine derivative.

2. The nanodevice of claim 1 wherein the small molecule to be delivered is a prodrug.

3. The nanodevice of claim 2 wherein the at least one small molecule to be delivered comprises theophylline or a derivative or salt thereof.

4. The nanodevice of claim 2 wherein the at least one small molecule comprises 1,3-dipropyl-8-cyclopentylxanthine or a derivative or salt thereof.

5. A method of making a nanodevice of claim 1 comprising:
   forming a gold nanoparticle having a surface;
   reacting the gold nanoparticle with a chemical agent to form functional groups on the surface of the gold nanoparticle;
   binding the gold nanoparticle to at least one molecule to be delivered; and
   crosslinking the gold nanoparticle to the targeting protein.

6. The method of claim 5 wherein the targeting protein comprises at least one variant of a plant lectin.

7. The method of claim 6 wherein the at least one molecule comprises a xanthine derivative.

8. The method of claim 7 wherein the at least one molecule comprises theophylline or a derivative or salt thereof.

9. The method of claim 7 wherein the at least one molecule comprises 1,3-dipropyl-8-cyclopentylxanthine or a derivative or a salt thereof.

10. The method of claim 5 wherein the gold nanoparticle is reacted with mercaptosuccinic acid to form functional groups on its surface.

11. A method of activating a crossed phrenic pathway in a patient using a nanodevice of claim 1, the nanodevice being delivered by at least one injection into a diaphragm of the patient.

12. The method according to claim 11 wherein the at least one injection consists of a single injection.

13. The method according to claim 12 wherein the nanodevice comprises theophylline or a derivative or salt thereof.

14. The method according to claim 12 wherein the nanodevice comprises 1,3-dipropyl-8-cyclopentylxanthine or a derivative or salt thereof.

15. The nanodevice of claim 1, wherein the nanodevice is retrogradely transported into a central nervous system of a mammal when injected into a diaphragm of the mammal.

16. The nanodevice of claim 15, wherein the nanodevice is transported transsynaptically.

17. The nanodevice of claim 1, wherein the at least one small molecule comprises theophylline or a derivative or salt thereof.

18. The nanodevice of claim 1, wherein the at least one small molecule comprises 1,3-dipropyl-8-cyclopentylxanthine or a derivative or salt thereof.

19. The nanodevice of claim 1, wherein the at least one small molecule comprises pro-theophylline.

20. The nanodevice of claim 1, wherein the at least one small molecule is attached to the gold nanoparticle via one of a fast-release linker and a slow-release linker.

* * * * *

UNITED STATES PATENT AND TRADEMARK OFFICE
CERTIFICATE OF CORRECTION

| | | |
|---|---|---|
| PATENT NO. | : 9,649,381 B2 | Page 1 of 1 |
| APPLICATION NO. | : 14/534994 | |
| DATED | : May 16, 2017 | |
| INVENTOR(S) | : Harry Goshgarian et al. | |

It is certified that error appears in the above-identified patent and that said Letters Patent is hereby corrected as shown below:

In the Specification

Column 1, Line 4, after the title, please insert:
-- FEDERALLY SPONSORED RESEARCH OR DEVELOPMENT
This invention was made with government support under grant number HD031550 awarded by The National Institutes of Health. The government has certain rights in the invention. --

Signed and Sealed this
First Day of August, 2017

Joseph Matal
*Performing the Functions and Duties of the*
*Under Secretary of Commerce for Intellectual Property and*
*Director of the United States Patent and Trademark Office*